(12) United States Patent
Gunday et al.

(10) Patent No.: US 10,349,977 B2
(45) Date of Patent: Jul. 16, 2019

(54) RESECTOR BALLOON CATHETER WITH MULTI-PORT HUB

(71) Applicants: Erhan H. Gunday, Great Neck, NY (US); Lawrence J. Gerrans, San Anselmo, CA (US); Alex Hsia, San Jose, CA (US); Devin J S Scheifele, San Mateo, CA (US); Jessie Tung, Cerritos, CA (US)

(72) Inventors: Erhan H. Gunday, Great Neck, NY (US); Lawrence J. Gerrans, San Anselmo, CA (US); Alex Hsia, San Jose, CA (US); Devin J S Scheifele, San Mateo, CA (US); Jessie Tung, Cerritos, CA (US)

(73) Assignee: Sanovas Intellectual Property, LLC, Reno, NV (US)

( * ) Notice: Subject to any disclaimer, the term of this patent is extended or adjusted under 35 U.S.C. 154(b) by 1349 days.

(21) Appl. No.: 13/837,970

(22) Filed: Mar. 15, 2013

(65) Prior Publication Data

US 2014/0275777 A1    Sep. 18, 2014

(51) Int. Cl.
*A61M 25/00* (2006.01)
*A61B 17/34* (2006.01)
(Continued)

(52) U.S. Cl.
CPC .......... *A61B 17/3439* (2013.01); *A61B 1/126* (2013.01); *A61B 17/320725* (2013.01);
(Continued)

(58) Field of Classification Search
CPC .......... A61M 25/1002; A61M 25/0097; A61B 17/3439; A61B 17/22; A61B 17/3205;
(Continued)

(56) References Cited

U.S. PATENT DOCUMENTS 4,726,374 A * 2/1988 Bales ................ A61M 39/0613
277/510
4,981,470 A    1/1991 Bombeck, IV
(Continued)

FOREIGN PATENT DOCUMENTS

WO    2012091364 A2    7/2012

OTHER PUBLICATIONS

International Search Report and Written Opinion of the International Searching Authority Application No. PCT/2014/024302 Completed: Aug. 29, 2014; dated Sep. 16, 2014 11 pages.
(Continued)

*Primary Examiner* — Timothy J Neal
(74) *Attorney, Agent, or Firm* — Forge IP, PLLC

(57) ABSTRACT

A catheter assembly includes a resector balloon catheter and a hub coupled to the proximal portion of the catheter. The hub includes an inflation port that supplies fluid to a first lumen of the catheter to inflate a resector balloon. The hub further includes a delivery port for delivering an agent, such as drugs, to a second lumen of the catheter for delivery to the distal end of the catheter. The hub also includes an aperture for inserting a device, such as an imaging device, into the second lumen of the catheter. In some embodiments, the catheter includes a third lumen, and the hub includes an additional port in fluid communication with the third lumen.

26 Claims, 16 Drawing Sheets

(51) Int. Cl.
*A61B 1/12* (2006.01)
*A61B 17/3207* (2006.01)
*A61F 7/12* (2006.01)
A61B 17/24 (2006.01)
A61B 17/22 (2006.01)
A61M 25/10 (2013.01)

(52) U.S. Cl.
CPC ......... *A61F 7/123* (2013.01); *A61M 25/0097* (2013.01); *A61B 17/24* (2013.01); *A61B 2017/22061* (2013.01); *A61F 2007/126* (2013.01); *A61M 2025/0008* (2013.01); *A61M 2025/109* (2013.01)

(58) Field of Classification Search
CPC ....... A61B 1/05; A61B 1/00082; A61B 1/126; A61B 1/015
USPC .......................... 600/104, 109, 153, 155, 157
See application file for complete search history.

(56) References Cited

U.S. PATENT DOCUMENTS

| | | | |
|---|---|---|---|
| 5,007,898 A | 4/1991 | Rosenbluth et al. | |
| 5,090,959 A | 2/1992 | Samson et al. | |
| 5,316,016 A | 5/1994 | Adams et al. | |
| 5,749,848 A | 5/1998 | Jang et al. | |
| 5,967,984 A | 10/1999 | Chu et al. | |
| 6,023,542 A | 2/2000 | Pan et al. | |
| 6,045,240 A | 4/2000 | Hochstein | |
| 6,102,929 A | 8/2000 | Conway et al. | |
| 7,198,397 B2 | 4/2007 | Bennett et al. | |
| 7,264,624 B2 | 9/2007 | Nash et al. | |
| 7,668,450 B2 | 2/2010 | Todd et al. | |
| 7,736,336 B2 | 6/2010 | Plishka et al. | |
| 7,914,517 B2 | 3/2011 | Baran et al. | |
| 7,988,633 B2 | 8/2011 | Hossack et al. | |
| 8,070,329 B1 | 12/2011 | Bechtel et al. | |
| 8,172,834 B2 | 5/2012 | Bhadri et al. | |
| 8,206,374 B2 | 6/2012 | Duane et al. | |
| 8,226,601 B2 | 7/2012 | Gunday et al. | |
| 8,246,230 B2 | 8/2012 | Todd et al. | |
| 2002/0077593 A1* | 6/2002 | Perkins et al. | 604/96.01 |
| 2004/0230116 A1 | 11/2004 | Cowan et al. | |
| 2005/0004504 A1* | 1/2005 | Frye et al. | 604/6.16 |
| 2005/0158687 A1 | 7/2005 | Dahm | |
| 2006/0282153 A1 | 12/2006 | Jang | |
| 2006/0293559 A1* | 12/2006 | Grice et al. | 600/102 |
| 2008/0077085 A1* | 3/2008 | Eidenschink et al. | 604/96.01 |
| 2008/0161890 A1* | 7/2008 | Lafontaine | 607/105 |
| 2009/0153797 A1 | 6/2009 | Allon et al. | |
| 2009/0154166 A1 | 6/2009 | Zhang et al. | |
| 2009/0192494 A1 | 7/2009 | Michishita et al. | |
| 2009/0264866 A1 | 10/2009 | Powell | |
| 2010/0121270 A1 | 5/2010 | Gunday et al. | |
| 2011/0057552 A1 | 3/2011 | Weaver | |
| 2011/0152683 A1 | 6/2011 | Gerrans et al. | |
| 2012/0120635 A1 | 5/2012 | Strong et al. | |
| 2012/0238816 A1 | 9/2012 | Gunday et al. | |
| 2012/0241781 A1 | 9/2012 | Yuan et al. | |
| 2012/0259217 A1 | 10/2012 | Gerrans et al. | |
| 2012/0291259 A1 | 11/2012 | Popovich et al. | |

OTHER PUBLICATIONS

International Search Report and Written Opinion of the International Searching Authority Application No. PCT/US2014/018948 Completed: Nov. 14, 2014; dated Dec. 8, 2014 7 pages.
International Search Report and Written Opinion of the International Searching Authority Application No. PCT/US2014/017539 Completed: May 19, 2014; dated Jun. 13, 2014 9 pages.

* cited by examiner

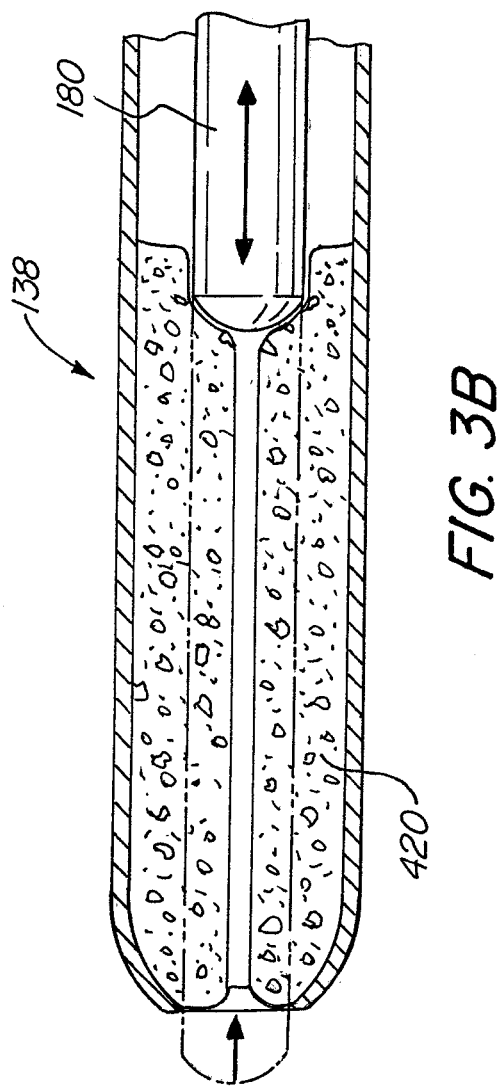

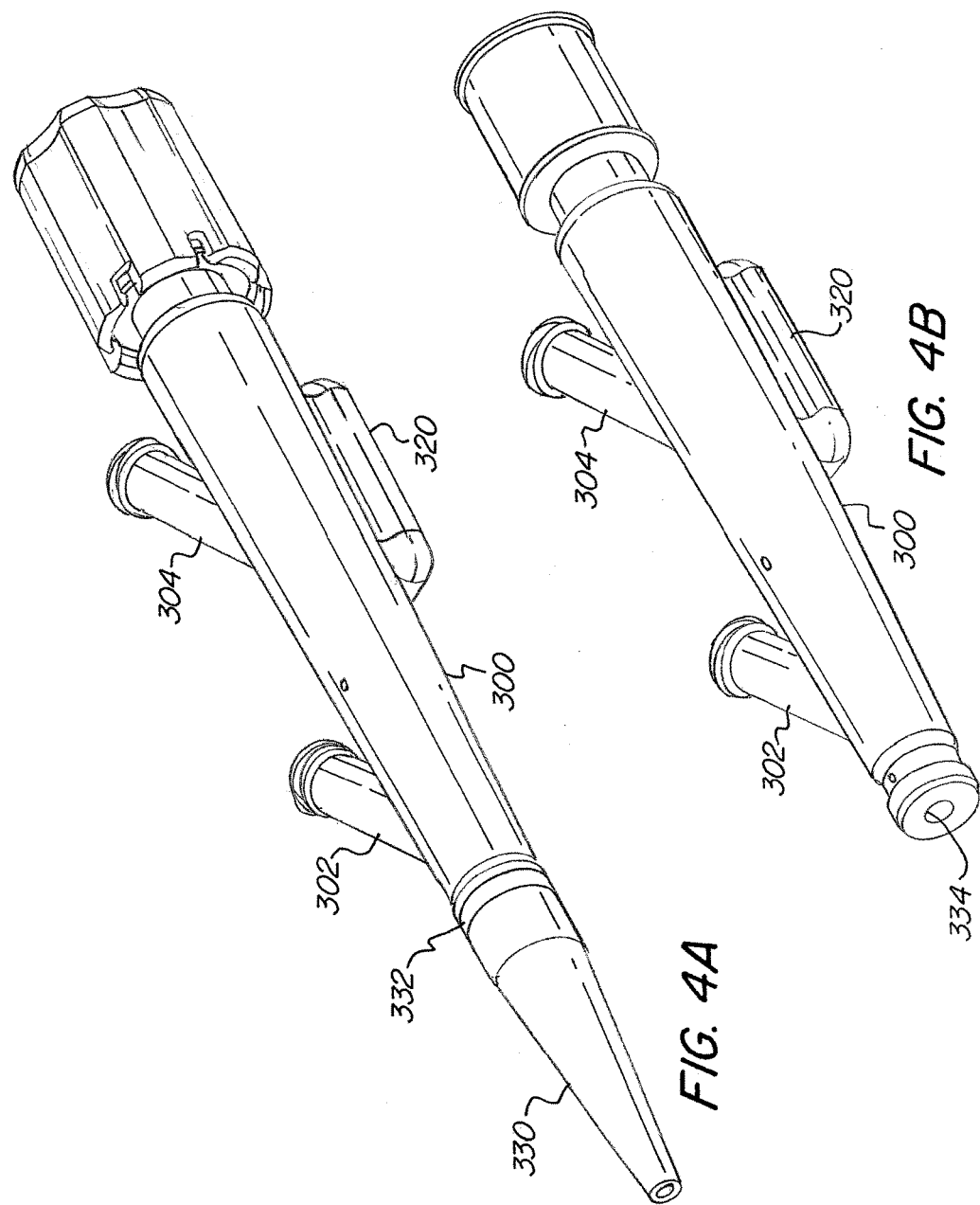

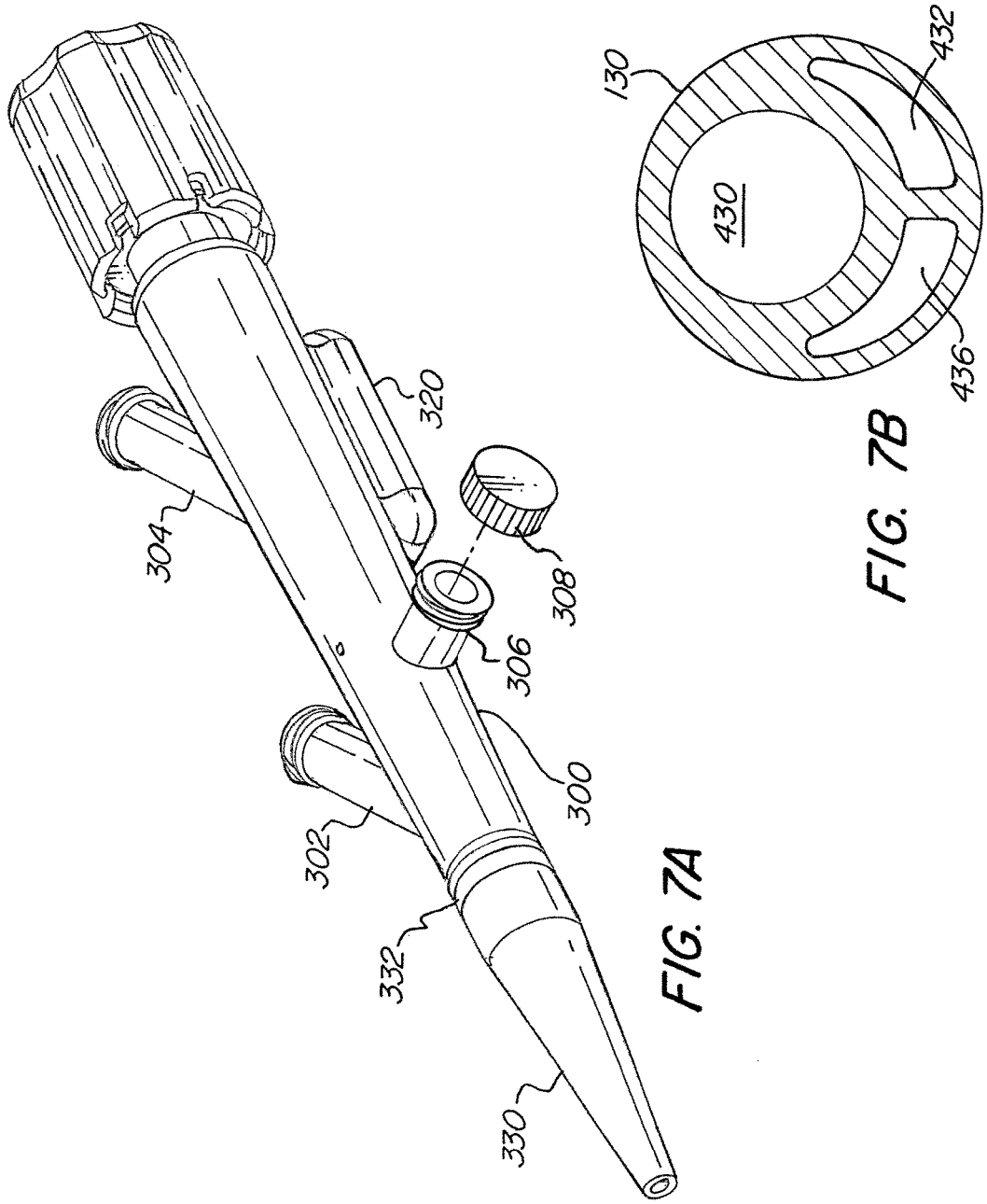

RESECTOR BALLOON CATHETER WITH MULTI-PORT HUB

FIELD OF THE INVENTION

The present invention relates to devices for the resection of unwanted biological material, such as tissue growths and tumors, in bodily cavities. More specifically, the invention relates to a balloon catheter with a multi-port hub for delivering fluids and devices to the anatomical target site.

BACKGROUND OF THE INVENTION

The removal of unwanted and/or life threatening biological material from interior portions of bodily cavities, such as organs, vessels, articular joints and structures, sinuses, and various bodily lumens, is a very common procedure in various medical specialties and disciplines, such as pulmonology, cardiology, urology, gynecology, gastro-enterology, neurology, otolaryngology, orthopedics, and general surgery. Accordingly, various instruments and methods have been employed to perform these procedures, which are generally well known in the art.

One of the most important complications in such procedures is bleeding. The bleeding and resulting morbidity of tissue that occurs in many of the currently known surgical procedures is the result of abrasive, traumatic, and invasive excising and removal techniques. Many of these techniques risk perforation of the vessel or lumen in which the procedure is being performed, resulting in grave complications for the surgeon and patient. In addition, many patient maladies are simply not remedied by these procedures because no interventional, minimally invasive treatment modality exists, the methods are not efficient, safe, and reproducible, and/or the instruments employed lack the appropriate visualization, physiological measurement, and/or feedback necessary to ensure the safety, efficacy, and reproducibility of the procedure. Accordingly, a new type of treatment is required.

One instrument that is commonly used in various types of medical procedures is an inflatable balloon catheter, of which many different types exist, which are utilized to perform various necessary functions. For example, these inflatable balloons are often used to control or stop bleeding, to hold instruments in place, or to prevent or facilitate other flow or movement within the bodily cavity. For example, many urological catheters are held in place via a balloon that impacts the sidewalls of the urinary tract, many gynecological instruments are held in place via balloons that impact the sidewalls of the vaginal vault, endovascular balloons are often used to control bleeding, inflatable balloons are sometimes used to control the backflow of radio-opaque agents injected into the cystic duct to detect the presence of gall stones during general surgical cholecystectomy procedures, and, recently, balloon catheters have been employed to release sinus congestion.

One particular application of such catheters is lung cancer. Among all types of cancer, this has the lowest survival rate, as more than one third of all deaths due to cancer are caused by lung cancer. Over 1.5 million new cases are diagnosed worldwide each year. The most frequent cause of death for lung cancer patients is airway obstruction. In lung cancer patients, one third of all cases initially, and another third of the cases in the long term, present main airway obstruction, which may cause asphyxia, hemorrhaging, and infection. These complications are the most frequent causes of death in lung cancer patients.

Use of interventional bronchoscopy for the treatment of lung cancer and the resultant airway obstruction increases the quality of life and survival rates of patients suffering from Chronic Obstructive Pulmonary Disease (COPD) and the obstructive co-morbidities associated with the cancer. Accordingly, balloon catheters have been routinely used with various endoscopes and with flexible and rigid bronchoscopes for dilation, as a tamponade to stop bleeding, and as an interference fixation device to hold instruments in place and prevent the retropulsion of those instruments under backflow pressure.

In light of the aforementioned need for a new type of treatment for removing undesirable biological material in bodily cavities, it has been realized that inflatable balloon catheters may further be employed as interventional tools for the excision and removal of such materials—such as endoluminal obstructions and tumors and endovascular occlusions—in various applications, such as the aforementioned interventional medical specialties of pulmonology, cardiology, urology, gynecology, gastro-enterology, neurology, otolaryngology, and general surgery. The use of balloon catheters in this way has presented a method of treatment that is simple, safe, highly effective, and inexpensive compared to other types of methods and devices that are used, such as mechanical, laser, electrocautery, cryotherapy, etc.

Accordingly, a new class of balloons has been suggested for this purpose, such as that disclosed in U.S. Pat. No. 8,226,601 to Gunday et al., the specification of which is hereby incorporated by reference herein in its entirety. This device employs a balloon catheter with an inflatable resector balloon. Using this device, one is able to treat obstruction in a bodily cavity by inserting the catheter with the balloon deflated into the bodily cavity. The balloon is aligned with the obstruction and then repeatedly inflated and deflated in pulsed fashion. The balloon's abrasive surface, when gradually pulsed in this way, gradually and non-traumatically resects the obstruction, while causing minimal damage to the surrounding, healthy tissue.

In order to accomplish this, the device must be inserted into a narrow and vital body cavity, such as a respiratory airway or coronary artery, and the doctor must conduct a precise procedure using the inserted device. Accordingly, it is desirable to have imaging available to provide the doctors with a view that facilitates precise positioning and operation of the device. Additionally, fluid must be continually supplied and withdrawn from resecting balloon in order for it to function. It is also desirable to deliver diagnostic and/or therapeutic agents to the target site to help diagnose and treat the pathology.

All of these features, of course, add to the complexity of the resection system. In order to accommodate them, the catheter must have multiple lumens. Furthermore, the catheter must remain as slim as possible to be able to enter narrow passages in the body. Finally, all of these devices and components (i.e., optics, pressurized fluid for the balloon, drugs) must be fed into the various lumens of the catheter from outside of the patient's body.

What is desired, therefore, is a resector balloon catheter for removing undesirable biological materials that is able to facilitate precise positioning an operation of the device. What is also desired is a resector balloon catheter that is able to facilitate diagnosis and/or additional treatment steps during the resection procedure. What is further desired is an assembly that provides balloon resection in a slim catheter.

SUMMARY OF THE INVENTION

Accordingly, it is an object of the present invention to provide a resector balloon catheter that also provides imaging of the target site.

It is a further object of the present invention to provide a resector balloon catheter that can deliver other fluids, in addition to the balloon inflation air, to the target site, such as diagnostic and/or therapeutic agents.

It is yet another object of the present invention to provide a resector balloon catheter that achieves the delivery of additional fluids and devices while maintaining simplicity and compactness.

In order to overcome the deficiencies of the prior art and to achieve at least some of the objects and advantages listed, the invention comprises a catheter assembly, including a hub having a proximal end and a distal end, a catheter with a proximal portion and a distal portion, wherein the proximal portion of the catheter is located at the distal end of the hub, and at least one balloon at the distal portion of the catheter, the balloon at least partially enclosing an inflation chamber and having a resecting surface for resecting biological material, wherein the catheter has a first lumen in fluid communication with the inflation chamber of the balloon, and a second lumen, and wherein the hub has an inflation port in fluid communication with the first lumen for supplying fluid to inflate the balloon, a delivery port in fluid communication with the second lumen for delivering an agent to the distal portion of the catheter, and an aperture for inserting a device into the second lumen.

In certain advantageous embodiments, the invention further comprises an imaging device disposed in the aperture of the hub and the second lumen of the catheter.

In some embodiments, the hub comprises a housing coupled to the catheter, and the inflation port and the delivery port are integrally formed with the housing. In certain embodiments, the aperture for inserting a device into the second lumen is at the proximal end of the hub.

In some embodiments, the first lumen is an outer lumen and the second lumen is an inner lumen.

In certain advantageous embodiments, the hub comprises a protuberance for mounting the hub to an inflation device. In some of these embodiments, protuberance includes an indicator corresponding to at least one characteristic of the catheter and/or balloon. In some cases, the indicator comprises an RFID tag. In other cases, the indicator comprises a laser bar code.

In some embodiments, the invention further comprises a band affixed to the hub with an indicator corresponding to at least one characteristic of the catheter and/or balloon. In some of these embodiments, the indicator comprises a color.

In certain embodiments, the invention further comprises a sealing member that seals the aperture when a device is disposed therein. In some of these embodiments, the sealing member comprises a silicone plug disposed in the aperture, and the proximal end of the hub comprises a threaded portion, further comprising a screw adjacent the plug that screws into the threaded portion of the hub and deforms the plug to seal the aperture around the device disposed therein, the plug and the screw each having a hole therethrough for accommodating the device. In some of these cases, the invention further comprises a knob mounted to the screw for turning the screw, the knob having a hole therethrough for accommodating the device.

In certain advantageous embodiments, the invention further comprises a strain relief mounted to the distal end of the hub around the proximal portion of the catheter.

In some embodiments, the resecting surface comprises a mesh affixed to the outer surface of the balloon. In certain cases, the mesh comprises elastane.

In certain embodiments, the hub comprises a housing having a channel defined by a wall that receives the proximal portion of the catheter, at least one glue hole located proximally of the inflation port for injecting glue between the channel wall and the catheter, and at least one glue hole located distally of the inflation port for injecting glue between the channel wall and the catheter.

In some embodiments, the invention further comprises a cleaning member at the distal portion of the catheter for cleaning an imaging device, wherein the cleaning member includes a flexible material at least partially occluding the second lumen such that the imaging device displaces at least some of the flexible material when moved therethrough. In some of these embodiments, the cleaning member comprises a plurality of flexing flaps at least partially occluding the conduit.

In some embodiments, the catheter includes gradation marks for indicating the distance the catheter is advanced into a bodily cavity. In certain embodiments, the catheter includes at least one imaging marker, and in some case, the at least one imaging marker includes a plurality of radio-opaque rings.

In certain advantageous embodiments, the catheter has a third lumen in fluid communication with the inflation chamber of the balloon, and the hub has an additional port in fluid communication with the third lumen.

BRIEF DESCRIPTION OF THE DRAWINGS

FIGS. 3B-D are isometric views of the cleaning member of the catheter in the assembly of FIG. 1.

FIG. 4A is an isometric view of the hub in the assembly of FIG. 1.

FIG. 4B is an isometric view of the hub of FIG. 4A without a strain relief or sealing mechanism.

FIG. 7A is an isometric view of a hub for use in the assembly of FIG. 1.

FIG. 7B is a cross-sectional view of a catheter for use with the hub of FIG. 7A.

DETAILED DESCRIPTION OF THE INVENTION

Figure 1A:
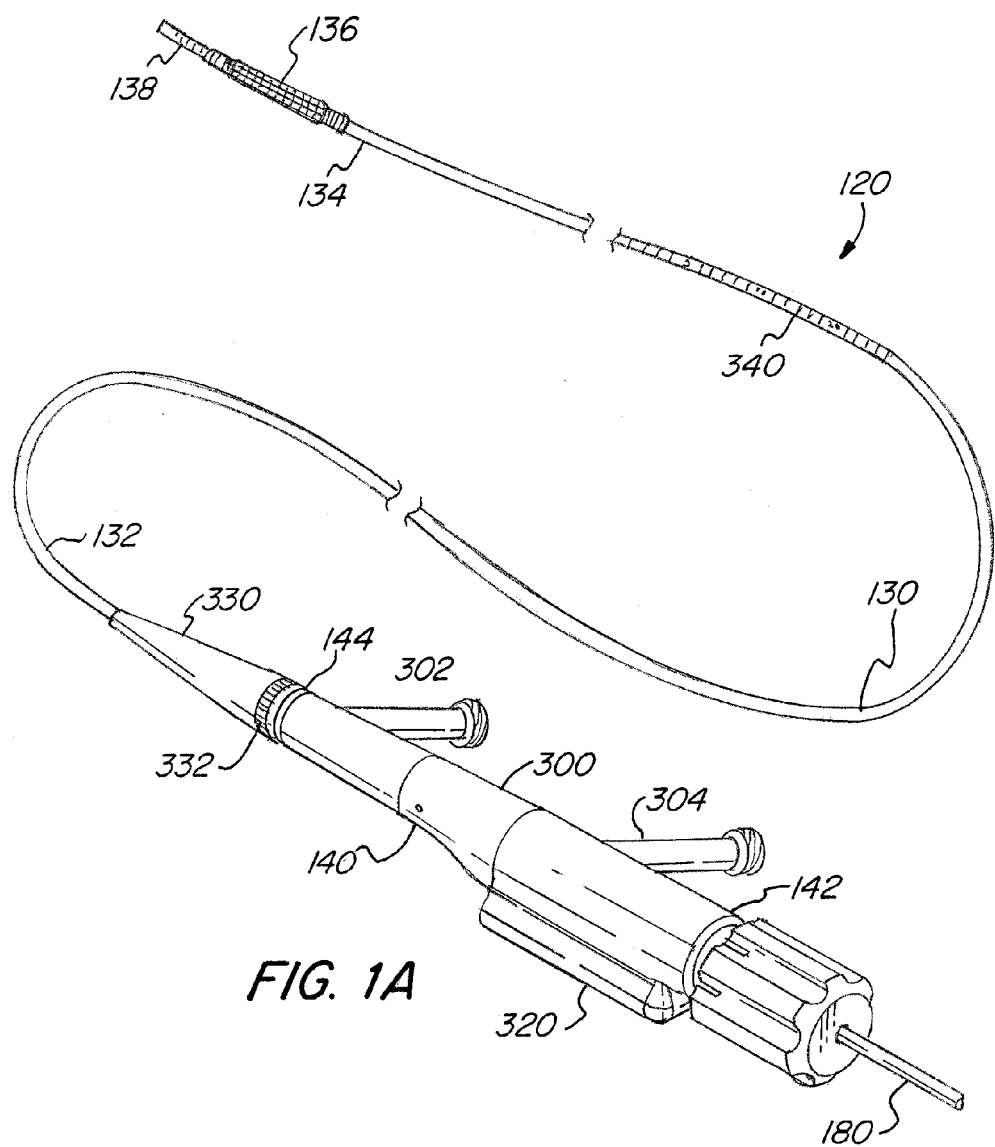
FIGS. 1A-B are isometric views of a catheter assembly in accordance with the invention.

The basic components of one embodiment of a resector balloon system in accordance with the invention are illustrated in FIG. 1. As used in the description, the terms "top,"

"bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

Figure 1B:
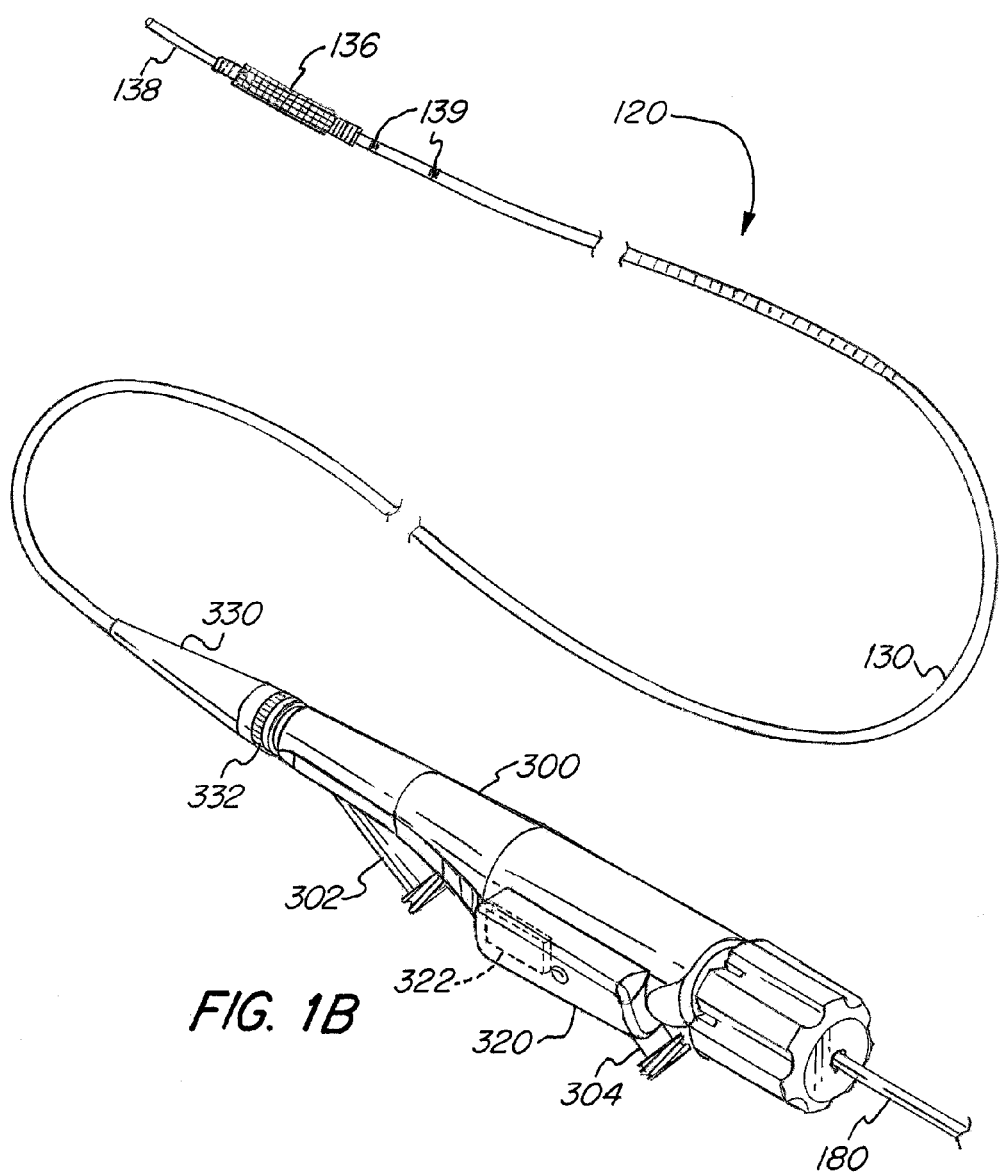

As shown in FIGS. 1A-B, the assembly (120) includes a hub (140) and a catheter (130). The catheter (130) has a proximal portion (132) and a distal portion (134). The hub (140) includes a housing (300), which has a proximal portion (142) and a distal portion (144) to which the proximal portion (132) of the catheter (130) is coupled. The distal portion (134) of catheter (130) includes an inflatable balloon (136), which has a textured surface on the outer wall thereof for resecting biological material, as described in Gunday et al.

In certain advantageous embodiments, this resecting surface is a mesh affixed to the balloon (136). In addition to resection, the textured surface assists in precisely guiding and positioning the device by ensuring that the balloon does not slip, and also ensures more uniform expansion of balloon (136) upon inflation. The mesh may be made of elastane, latex, polyurethane, composite springs, metallic fibers, elastic, steel fibers, cotton yarn, or other appropriate material, or a composite or coating thereof. A mesh sleeve may be disposed on the outer surface of balloon (136) by using any suitable manufacturing method. Alternatively, the mesh may be knitted or woven from thread directly onto balloon (136). In other advantageous embodiments, dimensional surface structures, such as bumps or inflatable sinuses that are encapsulated in the surface substrate of the balloon (136), may be used to produce surface protrusions that form the textured surface, such as is disclosed in U.S. Published Patent Application No. 2011/0152683 by Gerrans et al.

Figure 2A:
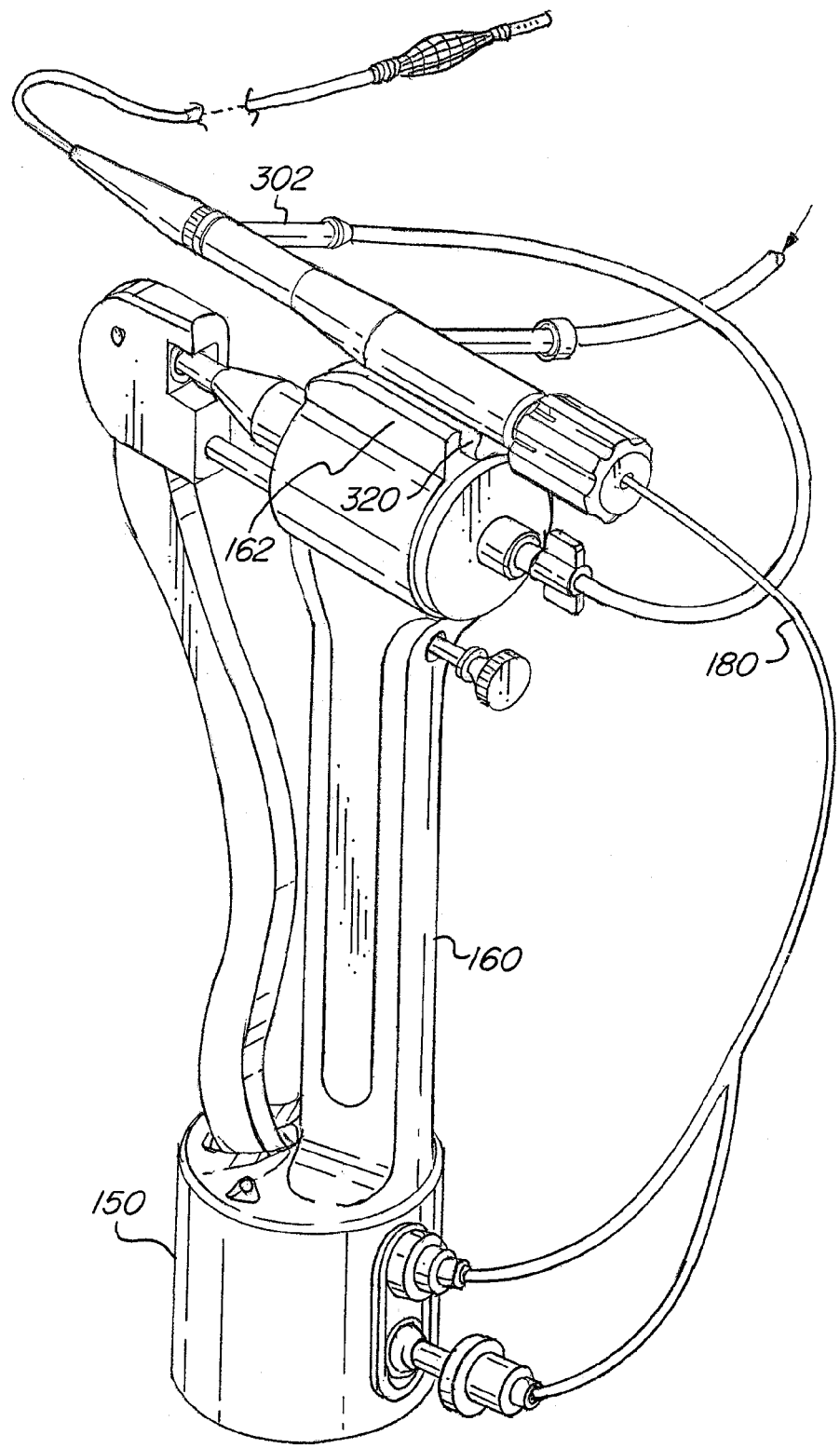
FIG. 2A is an isometric view of the catheter assembly of FIG. 1 mounted to a hand pump.
Figure 2B:
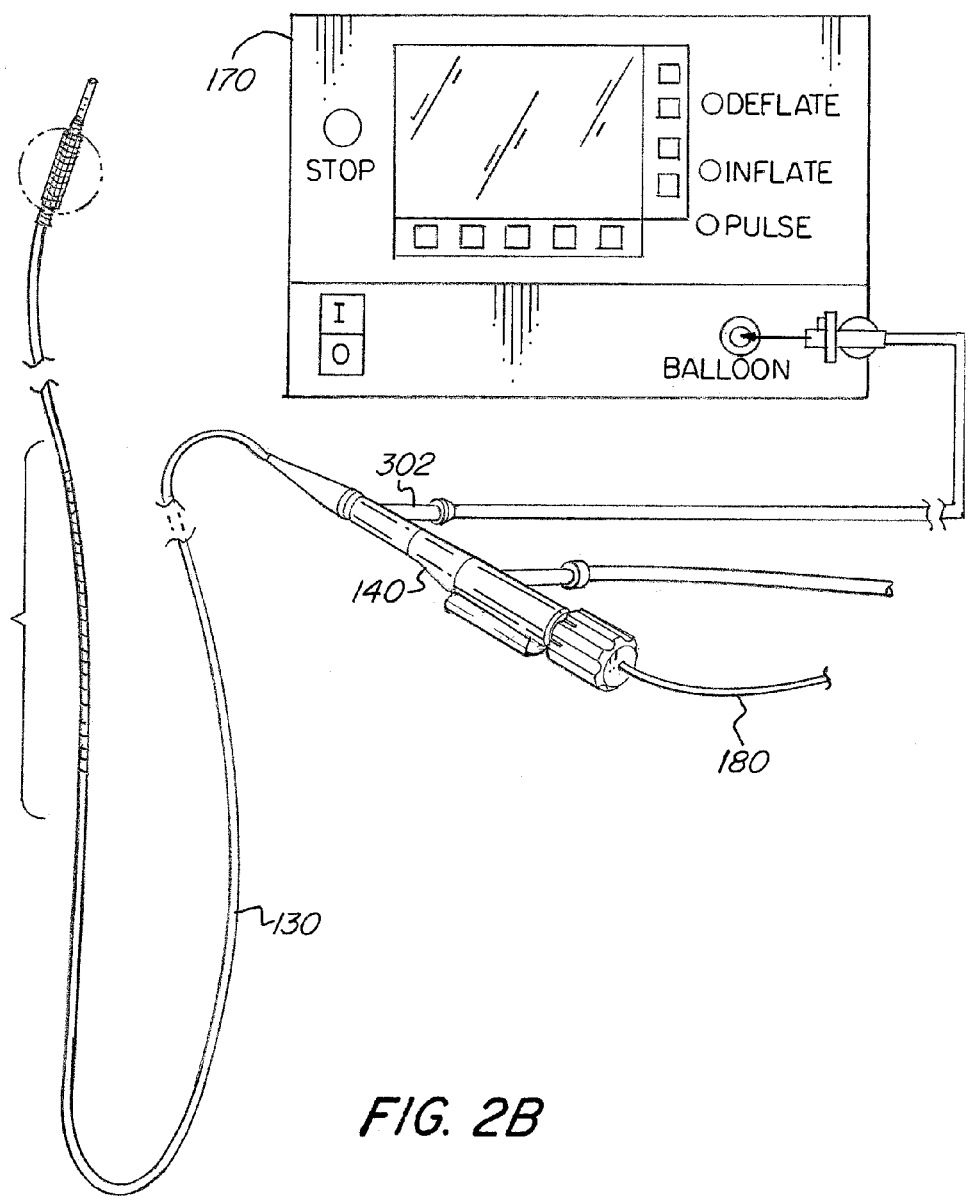
FIG. 2B is an isometric view of the catheter assembly of FIG. 1 connected to an electro-pneumatic pump.

The hub (140) includes an inflation port (302), to which a fluid source is coupled in order to supply fluid, such as air, to inflate the balloon (136). As shown in FIG. 2A, the fluid source may include a hand pump (160) that supplies air to the inflation port (302). Alternatively, as shown in FIG. 2B, the fluid source may be an electro-pneumatic pump (170), which likewise supplies air to the inflation port (302).

The hub (140) also includes a delivery port (304), to which another source is coupled, in order to deliver a fluid to the target site. This may be a source of a diagnostic and/or therapeutic agent, such as, for example, a syringe with a pre-measured amount of a drug.

The inflation port (302) and the delivery port (304) shown in FIGS. 1A-B are integrally formed with the housing (300). Additionally, the housing (140) includes a protuberance (320) for mounting the hub (140) to an inflation device. For example, the protuberance may be engaged by a clamp (162) on the hand pump (160) shown in FIG. 2A.

In certain embodiments, the protuberance (320) of the hub (140) includes an indicator (322) corresponding to a characteristic of the catheter (130) and/or balloon (136). For example, the indicator may indicate the diameter of the catheter (130), or the maximum inflation diameter, volume, or pressure of the balloon (136). This information may be computer-readable, thereby allowing another device, such as pump 160, to determine these characteristics. The indicator (322) may be, for example, an RFID tag, a 2D laser barcode, a magnetic strip, a memory device, or the like, which may be readable by the pump (160). As a result, the pump (160) or other medical equipment can use the proper settings during a medical procedure, such as a maximum pressure, so as not to allow over-inflation and popping of the balloon (136).

Figure 3A:
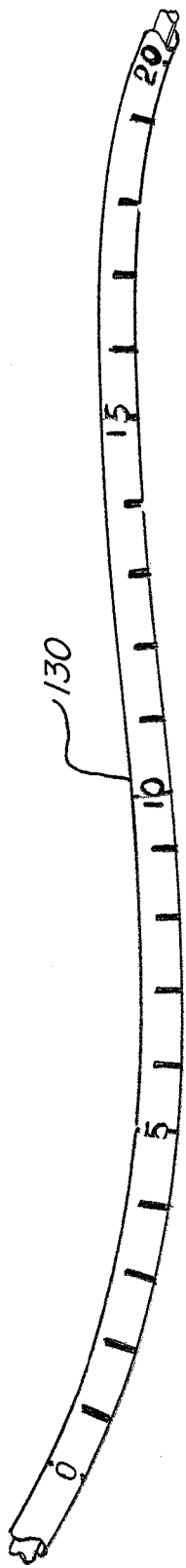
FIG. 3A is an isometric view of the catheter in the assembly of FIG. 1.
Figure 3C:
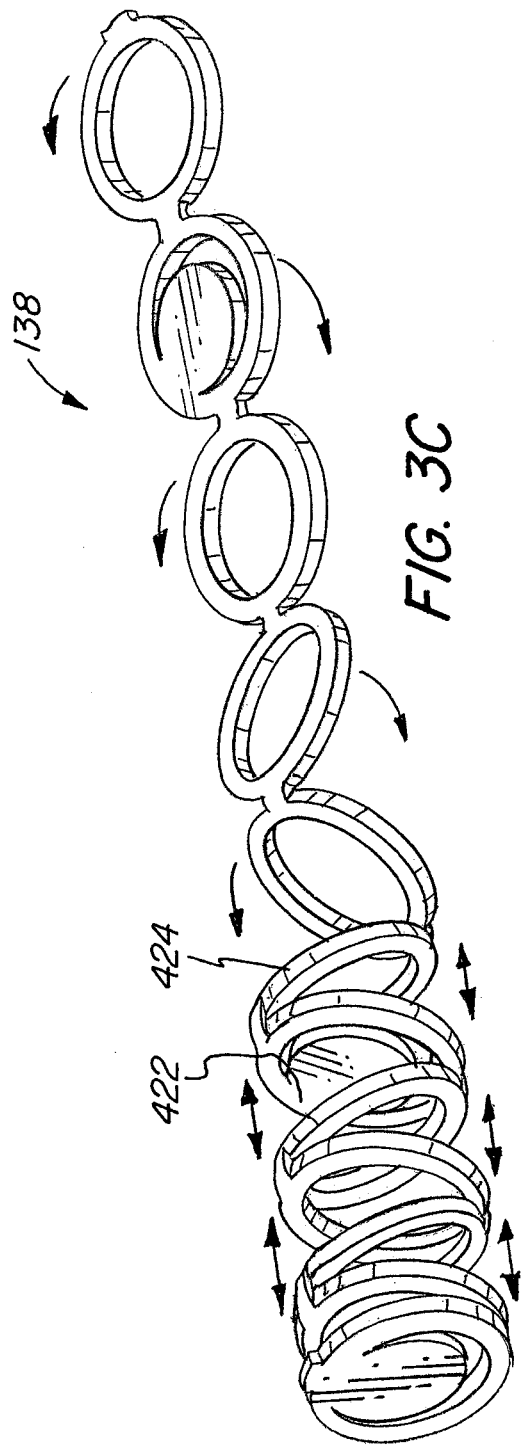
Figure 3D:
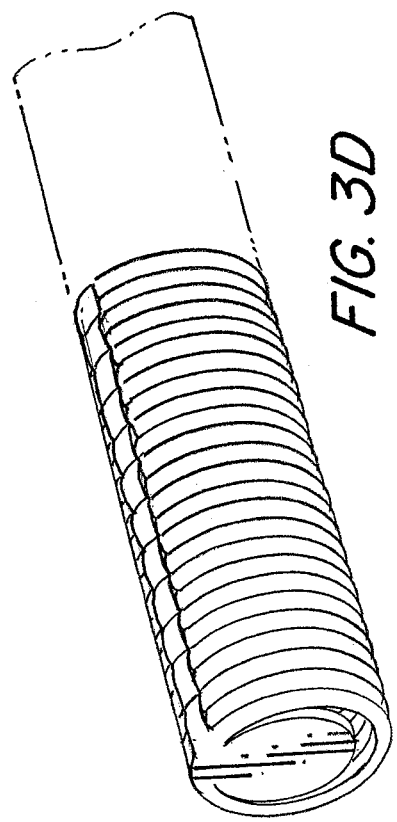

The catheter (130) includes gradation markings (340), which are also shown in greater detail in FIG. 3A. This permits the medical practitioner to more easily ascertain the depth to which the catheter (130) is inserted into a bodily cavity at any given time during a procedure. Catheter (130) also includes one or more imaging marker (139), such as radio-opaque rings, to facilitate external imaging.

A stress reliever, such as strain relief (330), is mounted to the distal end (144) of said hub (140). As shown in greater detail in FIGS. 4A-C, the strain relief (330) is placed over an aperture (334) in the housing (300) that receives the catheter (130), where there is a rigid right angle between the catheter and the surface of the housing (300) through which the aperture (334) passes. By covering the coupling of the catheter (130) to the housing (300) in this way, the strain relief (330) prevents the catheter (130) from kinking in this location during use. In some embodiments, a band (332) is affixed to the strain relief (330) and/or housing (300). The band (332) includes an indicator, such as a color, that corresponds to a characteristic of the catheter (130) and/or balloon (136), such as the diameter of the catheter (130), or the maximum inflation diameter, volume, or pressure of the balloon (136). As a result, a medical practitioner is able to quickly choose the correct balloon catheter for a given procedure.

Figure 4C:
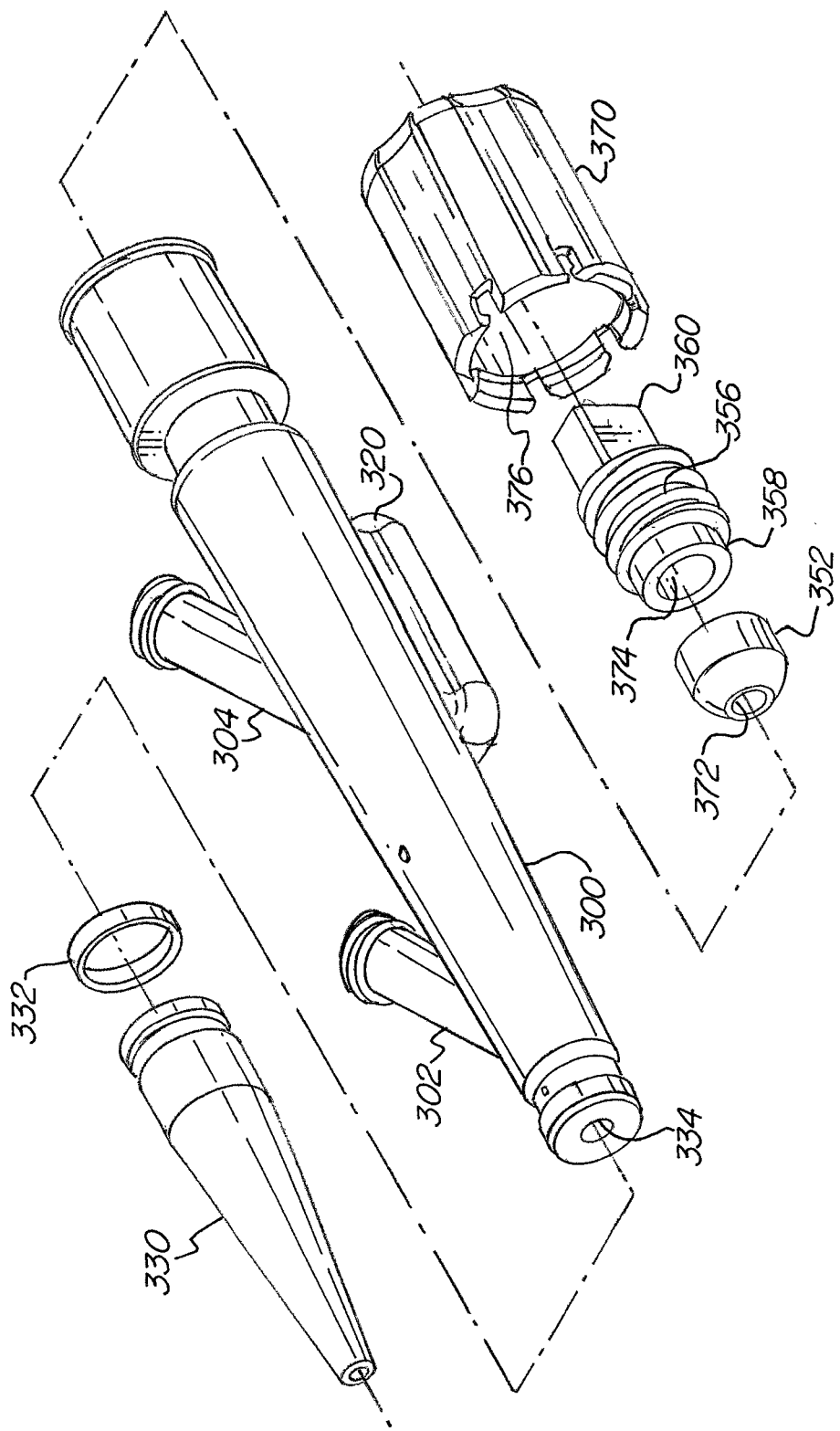
FIG. 4C is an exploded view of the hub of FIG. 4A.
Figure 5A:
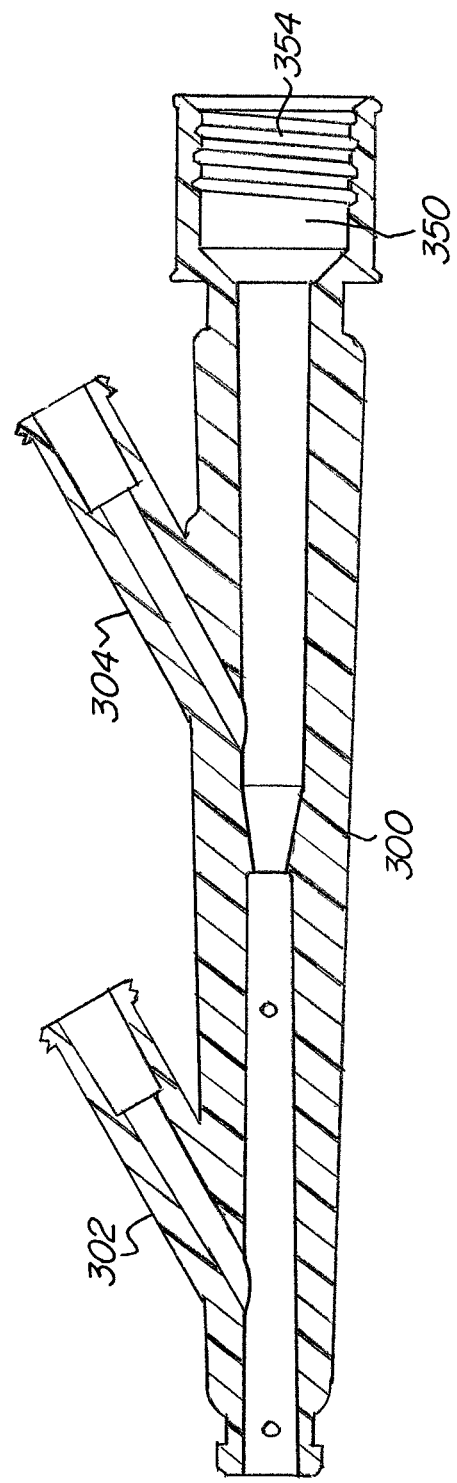
FIG. 5A is a partially cross-sectional, plan view of the hub of FIG. 4B.
Figure 5B:
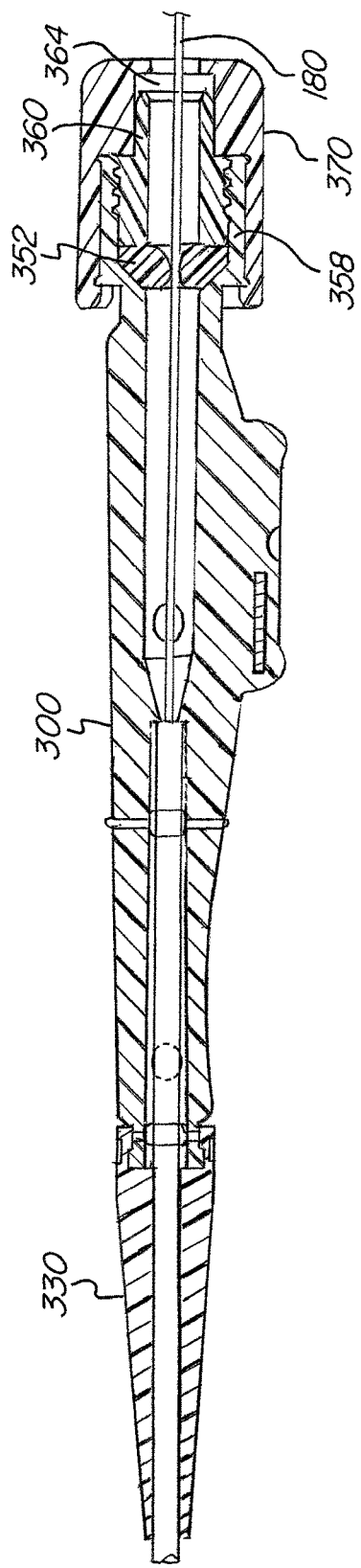
FIG. 5B is a partially cross-sectional, elevation view of the hub of FIG. 4A.

As also shown in FIGS. 4A-C, as well as FIGS. 5A-B, the proximal portion (142) of the hub (140) includes an aperture (350) for inserting a device, such as an imaging device (180), through the rear of the hub (140). A sealing member, such as a silicone plug (352), is disposed in the aperture (350) to seal in order to seal it after the imaging device (180) is inserted. The aperture (350) includes threads (354), which mate with the threads (356) of a screw (358). The screw (358) has a protrusion (360) that fits into a corresponding seat (364) of a knob (370). The plug (352), screw (358), and knob (370) each have a hole (372, 374, 376) therethrough to accommodate the imaging device (180). Once the device (180) is inserted through the holes (372, 374, 376) and into the housing (300), the knob (370) is turned, which turns the screw (358) into the threaded aperture (350). As the screw (358) presses against the plug (352), the plug (352) is compressed and deforms so as to seal the aperture (350) around the device (180). It should be noted that, although a screw (358) has been described, any driver for exerting a force of the plug (352) in order to seal the aperture (350) around the device (180) may be employed.

Figure 6A:
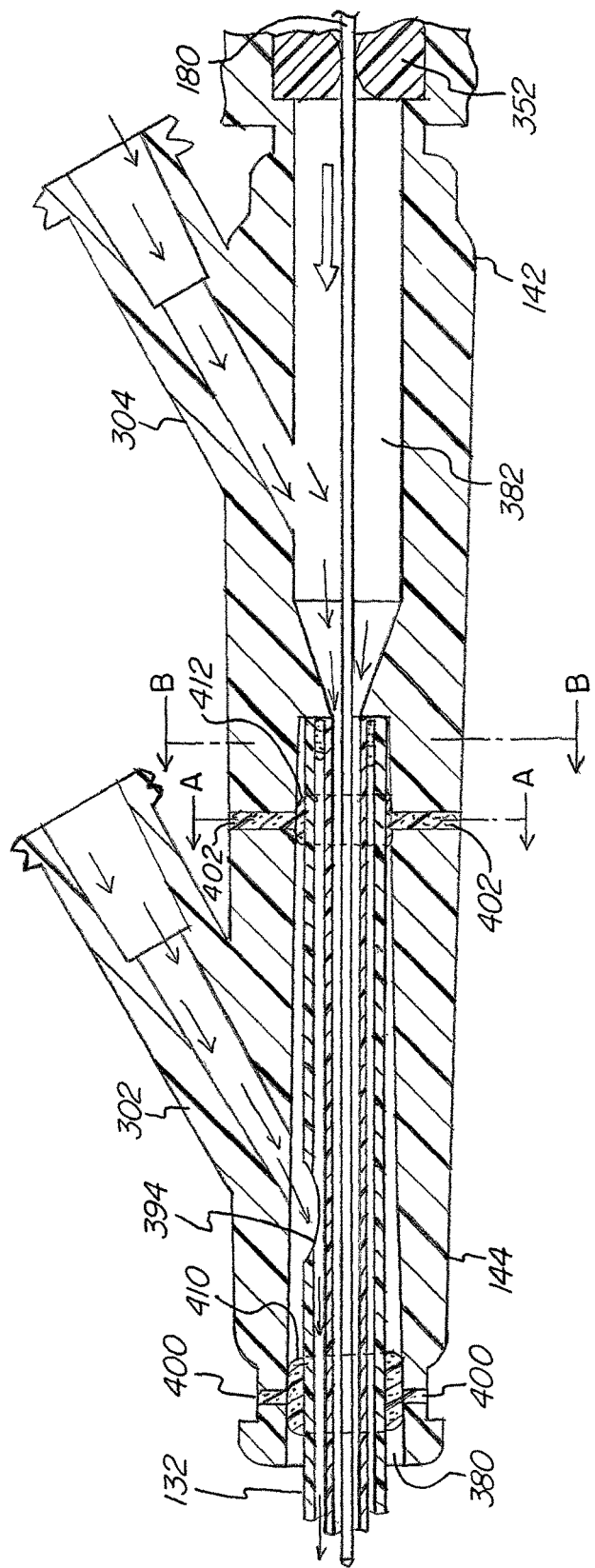
FIG. 6A is cross-sectional plan view of a portion of the hub of FIG. 4B.
Figure 6B:
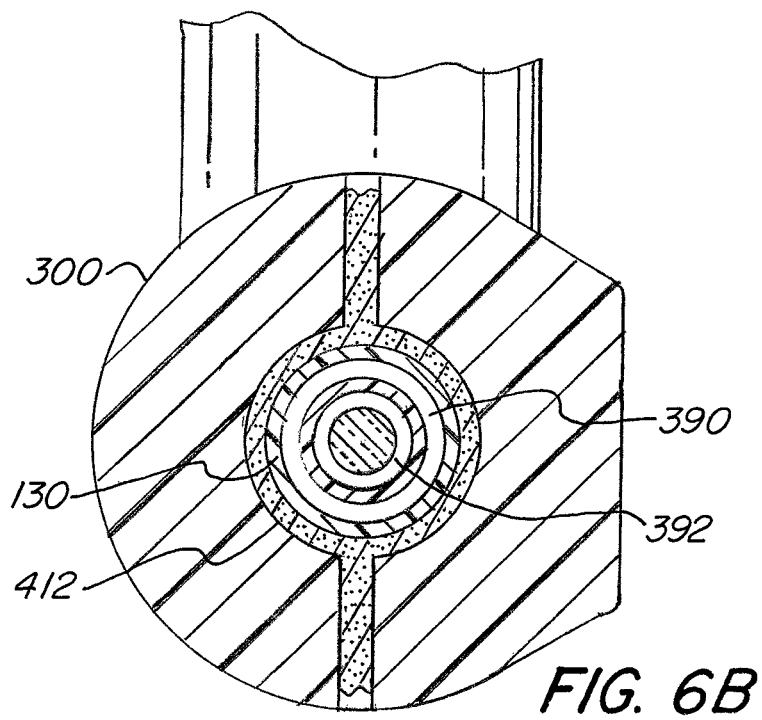
FIG. 6B is a cross-sectional view of the hub of FIG. 6A taken along line A-A.
Figure 6C:
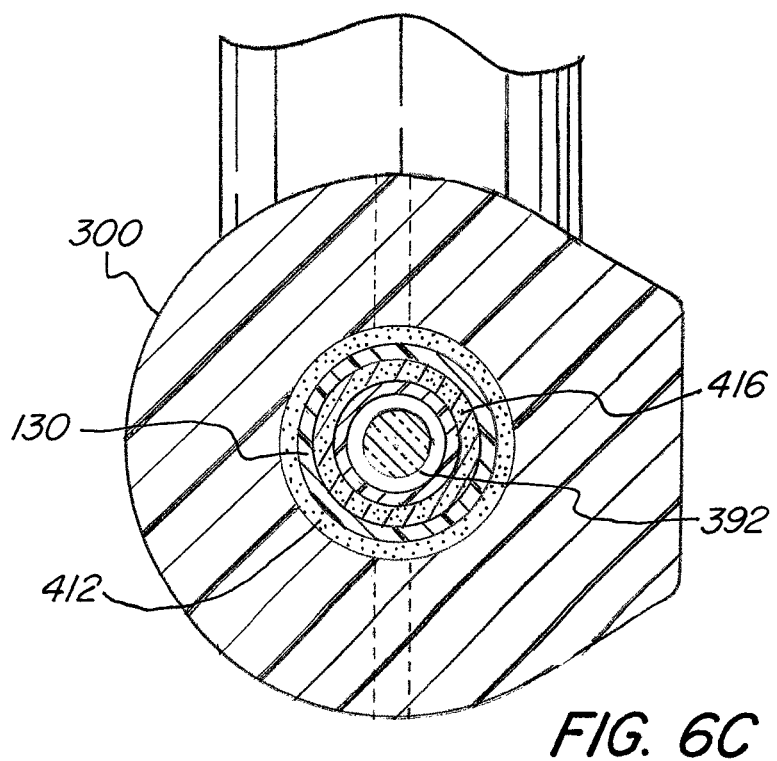
FIG. 6C is a cross-sectional view of the hub of FIG. 6A taken along line B-B.

As shown in FIGS. 6A-C, the proximal end (132) of catheter (130) is disposed in a channel (380) in the distal end (144) of the hub housing (300). The catheter (130) includes an outer lumen (390), which is in fluid communication with the interior of balloon (136), and an inner lumen (392) that also extends to the distal end of the catheter (130). The catheter (130) includes an aperture (394) that opens into the outer lumen (390), such that the inflation port (302) is in fluid communication with the outer lumen (390) and the inflation chamber of the balloon (136). As a result, a fluid source, such as pump (160), can supply fluid, such as air, to the balloon (136) to inflate it.

In order to channel the inflation air to the outer lumen (390) at a desired pressure, the housing (300) includes glue holes for providing a seal between the wall of the hub channel (380) and the catheter (130). Specifically, the housing includes glue holes (400) located distally of the inflation port (302), and glue holes (402) located proximally of the inflation port (302), for injecting glue between the wall of the hub channel (380) and the catheter (130). This produces a glue seal (410) distal of the inflation port (302) and glue seal (412) proximal of the port (302).

Thus, the catheter assembly (120) can be conveniently constructed by inserting catheter (130) into the aperture (334) and channel (380) of the hub housing (330), and subsequently injecting glue into glue holes (400, 402). Glue seals (410, 412) both help to retain catheter (130) in hub (140) and prevent the escape of pressurized fluid when it is supplied via the inflation port (302). Specifically, distal glue seal (410) prevents escape of pressurized fluid from the distal end of housing (300), and proximal glue seal (412) prevents the escape of pressurized fluid into channel (382) at the proximal portion (142) of hub (140).

FIGS. 6B and 6C show cross-sections of hub (140) taken along lines A-A and B-B in FIG. 6A. FIG. 6B shows a view from the location of proximal glue holes (402), where glue seal (412) has formed around catheter (130). FIG. 6C shows a view from the location where the outer lumen (390) of catheter (130) itself is sealed. Here, seal (416) prevents the escape of pressurized fluid from outer lumen (390) through the proximal tip of catheter (130) and into channel (380).

The delivery port (304) is in fluid communication with the channel (382) of hub housing (300) and inner lumen (392) of catheter (130). As a result, various diagnostic and/or therapeutic agents may be delivered into the inner lumen (392) and to the distal end of catheter 130. Such agents can be delivered directly to the target site, and can be supplied through the delivery port (304) continuous, periodic, and/or timed release.

As explained above, housing (300) also includes an aperture (350) at the proximal end thereof, and in certain advantageous embodiments, an imaging device (180) is inserted therein. When sealing member (252) is compressed by a driver (358), it expands inwardly toward the center of the aperture (350), resulting in a tightening around imaging device (180). As the components enter a fully closed position, imaging device is securely fixed in place by the compressed plug (252), which also creates a seal around it. By reversing this process, the seal can be loosened so that the imaging device may be moved, and then tightened again.

The imaging device (180) can be advanced out the distal end of catheter (130), allowing a user to shine light on the target site and view the reflected light from the body cavity. However, moving the imaging device (180) out of the catheter can cause it to become covered with biological material, which obstructs the practitioner's view. In order to remedy this problem, the distal portion of (134) of catheter (130) includes a cleaning element (138), as shown in FIGS. 1A-B.

As illustrated in FIG. 3B, the cleaning (138) element may, for example, comprise a porous material (420), charged with a cleaning solution. As another example, the cleaning member (138) may comprise a series of flexing flaps (422) with spacers (424) separating them. Any suitable cleaning member (138) may be employed, such as those described in U.S. Published Patent Application No. 2012/0238816 by Gunday et al., the specification of which is hereby incorporated herein in its entirety. The imaging device (180) can be partially retracted into catheter (130) such that the lens or other optical element at the end of the device can be pushed through the cleaning element (138) to wipe all materials from the surface of the device. This allows a medical practitioner to clean the tip of the imaging device (180) during a procedure by retracting and re-advancing the distal tip of the imaging device (180) so that the operator can then continue the procedure with a clear view. This action can be periodically performed during a surgery as necessary to maintain a clear view.

The inner lumen (392) of catheter (130) can be used to deliver any number of things to assist with opening the cavity, circulation, aspiration, respiration, assisting the decomposition of an obstruction, or stimulating healing in the affected area, including air, aspirates, drugs, biologics, biogenetic agents, nano-particulates, solutions, stem cell and gene therapies, and stents and scaffolds. Specifically, the device could be used for the deployment and implantation of pro-generative vehicles and/or catalysts in the repair, treatment, and therapy of the targeted areas, including biologic, nano-particulate materials and/or biogenetic materials, structures, scaffolds, and similar devices and vehicles, including, for example, bone morphogenetic proteins, microcrystalline nano-particulates, collagens, de-mineralized bone chips, calcium based structures, poly glycolic acids, poly lactic acids, and hyaluronic acids. The device can likewise be used for the deployment and implantation of inert, inelastic, and semi-rigid materials, such as, for example, PEEK, ceramic, cobalt chrome, titanium, and stainless steel, and for the implantation of reinforcing constructs within, along, and/or around anatomic structures, which may be deployed and then impregnated, impacted, and otherwise filled, either prior to or after insertion, with inert materials including, for example, polymethyl methacrylate, bone cements, polyethylene, polypropylene, latex, and PEEK.

Figure 7C:
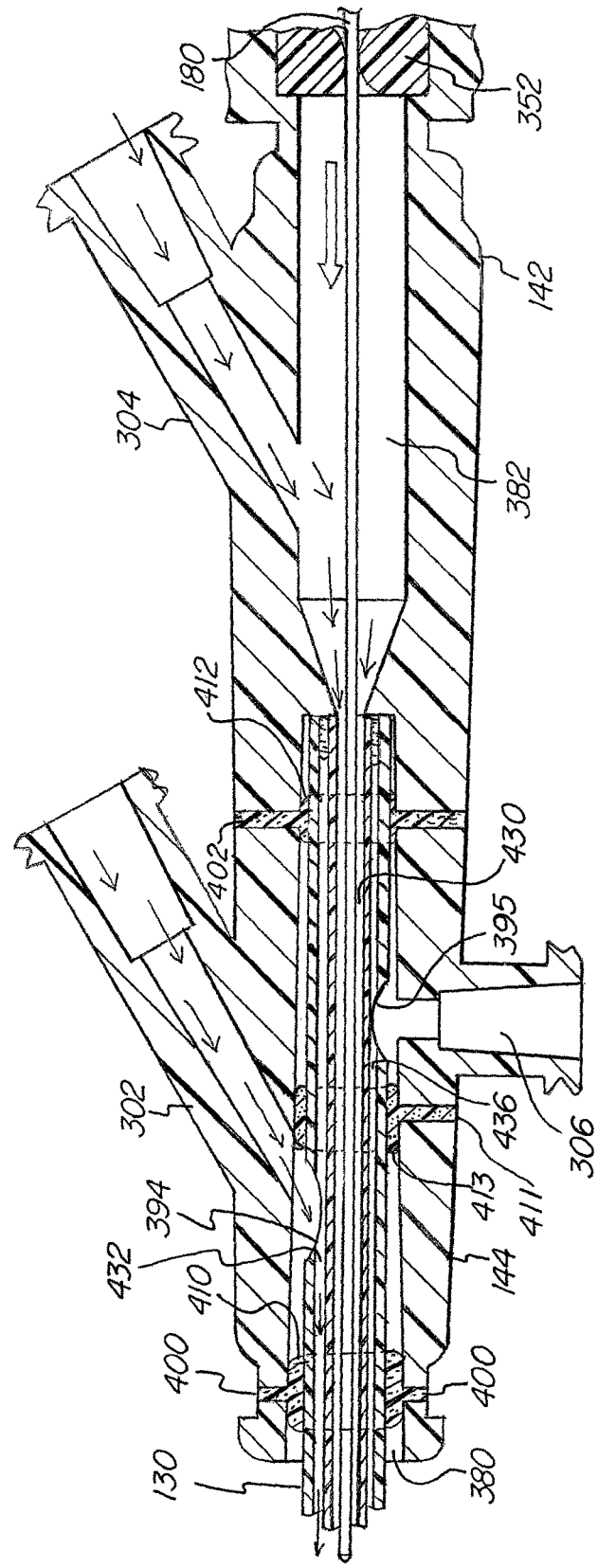
FIG. 7C is cross-sectional plan view of the hub of FIG. 7A.

As shown in FIGS. 7A-B, in certain advantageous embodiments, the catheter (130) has a dual inflation lumen structure instead of outer lumen (390) and the housing (300) includes a second inflation port (306). Referring to FIGS. 7B-C, fluid supplied into aperture (394) enters lumen (432) of the catheter (130). The wall of the proximal portion of the catheter (130) also includes another aperture (395), through which fluid is introduced into lumen (436). Additional glue holes (411) are provided for injecting glue between the catheter (130) and the wall of the hub channel (380) to create another seal (413), such the fluid supplied by ports (302) and (306) are isolated to lumen (432) and (436), respectively.

Figure 7D:
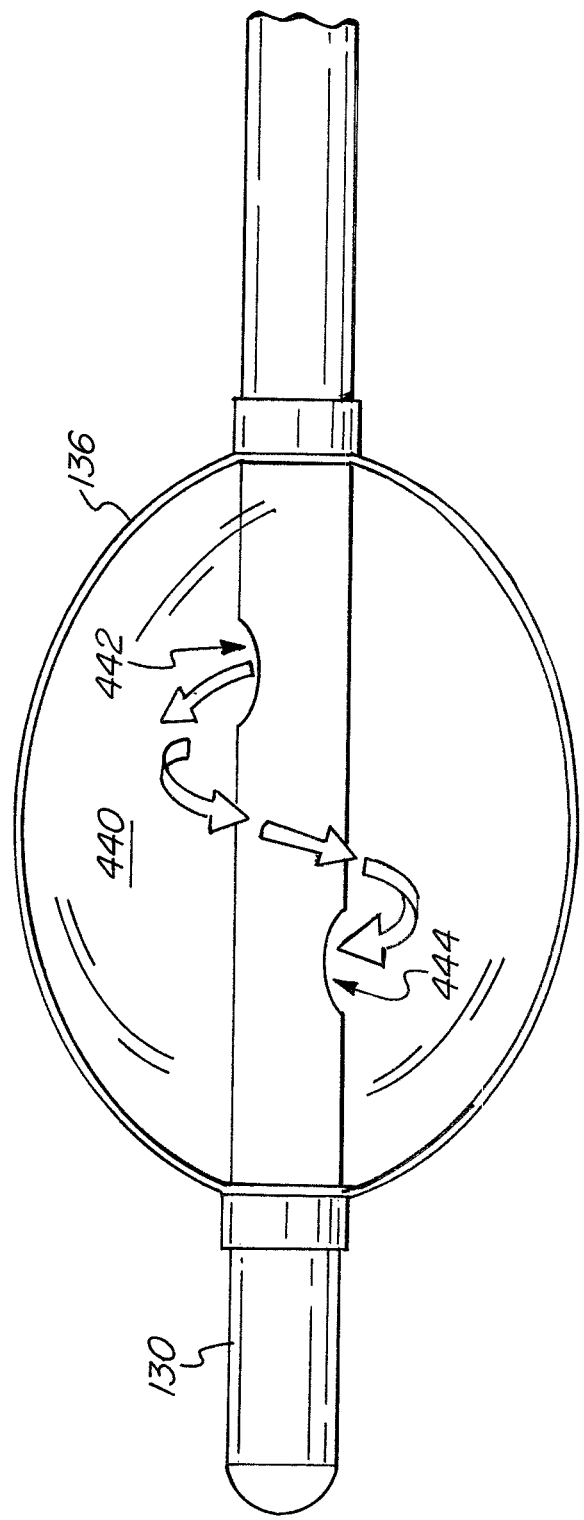
FIG. 7D is an isometric view of the distal portion of the balloon catheter of FIG. 7B.

As shown in FIGS. 7C-D, lumen (432) delivers fluid through aperture (442) in the wall of the distal portion of the catheter (130) and into the inflation chamber (440) of the balloon (136). Similarly, lumen (436) is in fluid communication with the inflation chamber (440) of balloon (136) via another aperture (444) in the wall of the distal portion of the catheter (130). This dual lumen structure is particular useful for various purposes.

In cases where the fluid being delivered to the inflation chamber (440) is a gas, such as air, both port (302) and port (306) can be used to supply the air simultaneously. This results in a significant increase of the cross sectional area, which increases the flow rate, while keeping the overall outer diameter of the catheter (130) as small as possible. Additionally, the additional port (306) can be used to flush air out of the system, which can be accomplished by introducing a liquid into the inflation port (302) and lumen (432) until the liquid begins to discharge from the additional inflation port (306). The additional inflation port can then be sealed with a cap (308), resulting in a system that is fully purged of air.

When the fluid being supplied is a liquid, such as water, and there is no need to maintain significant pressure within the system, the additional port (306) can remain open, such that the liquid can be circulated through the system, through lumen (432) and aperture (442), into the inflation chamber (440), back through aperture (444) and lumen (436), and out port (306). This can be particularly useful in applications where the temperature of the liquid in the balloon must be maintained, such as in bronchial thermoplasty, where it is desirable to heat the tissue. In order to accomplish this, heated water can be continuously delivered to the balloon (136) to heat the tissue. A fluid source can continuously supply new heated water to the balloon, or the water continuously being discharged from the port (306) can be run through a heating device and ultimately recirculated back into port (302).

The catheter also includes a lumen (430) for accommodating an imaging device (180) and agents delivered via delivery port (304), as previously described.

It should be understood that the foregoing is illustrative and not limiting, and that obvious modifications may be made by those skilled in the art without departing from the spirit of the invention. Although the invention has been described with reference to embodiments herein, those embodiments do not limit the scope of the invention. Accordingly, reference should be made primarily to the accompanying claims, rather than the foregoing specification, to determine the scope of the invention.

What is claimed is:

1. A catheter assembly, comprising:
   a hub having a proximal end and a distal end, a proximal hub channel in the proximal end of said hub, and a distal hub channel defined by a wall in the distal end of said hub;
   a catheter with a proximal portion and a distal portion, wherein the proximal portion of said catheter is disposed in the distal hub channel; and
   at least one balloon at the distal portion of said catheter, said balloon at least partially enclosing an inflation chamber and having a resecting surface for resecting biological material;
   wherein said catheter has an outer lumen in fluid communication with the inflation chamber of said balloon, and an inner lumen in fluid communication with the proximal hub channel; and
   wherein said hub has an inflation port in fluid communication with the distal hub channel for supplying fluid to inflate said balloon;
   a first seal between the wall of the distal hub channel and said catheter, proximal to the inflation port, and a second seal between the wall of the distal hub channel and said catheter, distal to the inflation port, such that the first seal and the second seal define a cavity therebetween;
   wherein said catheter includes an aperture between the first seal and the second seal such that fluid supplied to said hub through the inflation port flows into the cavity between said first and second seals, through the aperture, and into the outer lumen of said catheter;
   a delivery port in fluid communication with the proximal hub channel and proximal to said first seal, such that the delivery port is in fluid communication with the inner lumen of the catheter;
   wherein said hub includes an aperture proximal to the proximal hub channel for inserting a device into the proximal hub channel and into the inner lumen of the catheter.

2. The catheter assembly of claim 1, further comprising an imaging device disposed in the aperture of said hub and the inner lumen of said catheter.

3. The catheter assembly of claim 1, wherein said hub comprises a housing coupled to said catheter, and said inflation port and said delivery port are integrally formed with said housing.

4. The catheter assembly of claim 1, wherein the hub comprises a protuberance for mounting the hub to an inflation device.

5. The catheter assembly of claim 4, wherein the protuberance includes an indicator corresponding to at least one characteristic of said catheter and/or balloon.

6. The catheter assembly of claim 5, wherein the indicator comprises an RFID tag.

7. The catheter assembly of claim 5, wherein the indicator comprises a laser bar code.

8. The catheter assembly of claim 1, further comprising a band affixed to said hub with an indicator corresponding to at least one characteristic of said catheter and/or balloon.

9. The catheter assembly of 8, wherein the indicator comprises a color.

10. The catheter assembly of claim 1, further comprising a sealing member that seals the aperture proximal to the proximal hub channel when a device is disposed therein.

11. The catheter assembly of claim 10, wherein said sealing member comprises a silicone plug disposed in the aperture proximal to the proximal hub channel, and the proximal end of said hub comprises a threaded portion, further comprising a screw adjacent said plug that screws into the threaded portion of said hub and deforms the plug to seal the aperture around the device disposed therein, said plug and said screw each having a hole therethrough for accommodating the device.

12. The catheter assembly of claim 11, further comprising a knob mounted to said screw for turning said screw, said knob having a hole therethrough for accommodating the device.

13. The catheter assembly of claim 1, further comprising a strain relief mounted to the distal end of said hub around the proximal portion of said catheter.

14. The catheter assembly of claim 1, wherein the resecting surface comprises a mesh affixed to the outer surface of the balloon.

15. The catheter assembly of 14, wherein the mesh comprises elastane.

16. The catheter assembly of claim 1, further comprising a cleaning member at the distal portion said catheter for cleaning an imaging device, wherein said cleaning member includes a flexible material at least partially occluding the inner lumen such that the imaging device displaces at least some of the flexible material when moved therethrough.

17. The catheter assembly of claim 16, wherein said cleaning member comprises a plurality of flexing flaps at least partially occluding said inner lumen.

18. The catheter assembly of claim 1, wherein said catheter includes gradation marks for indicating the distance said catheter is advanced into a bodily cavity.

19. The catheter assembly of claim 1, wherein said catheter includes at least one imaging marker.

20. The catheter assembly of claim 19, wherein said at least one imaging marker includes a plurality of radio-opaque rings.

21. The catheter assembly of claim 1, wherein said catheter has a third lumen in fluid communication with the inflation chamber of said balloon, and wherein said hub has an additional port in fluid communication with said third lumen.

22. The catheter assembly of claim 1, wherein:

the first seal comprises glue;

said hub comprises at least one proximal glue hole, located proximally of the inflation port and catheter aperture and in communication with the distal hub channel, for supplying glue to a space between the wall of the distal hub channel and said catheter to form the first seal;

the second seal comprises glue; and said hub comprises at least one distal glue hole, located distally of the inflation port and catheter aperture and in communication with the distal hub channel, for supplying glue to the space between the wall of the distal hub channel and said catheter to form the second seal.

23. The catheter assembly of claim 22, wherein the at least one proximal glue hole comprises a plurality of proximal glue holes, and the at least one distal glue hole comprises a plurality of distal glue holes.

24. The catheter assembly of claim 21, further comprising:

a middle seal between the wall of the distal hub channel and said catheter, distal to the additional port and proximal to the inflation port;

wherein said catheter includes a second aperture between the first seal and the middle seal such that fluid flows between the additional port and the third lumen through the second catheter aperture.

25. The catheter assembly of claim 24 wherein:

the first seal comprises glue;

said hub comprises at least one proximal glue hole, located proximally of the inflation port and catheter aperture and in communication with the distal hub channel, for supplying glue to a space between the wall of the distal hub channel and said catheter to form the first seal;

the second seal comprises glue;

said hub comprises at least one distal glue hole, located distally of the inflation port and catheter aperture and in communication with the distal hub channel, for supplying glue to the space between the wall of the distal hub channel and said catheter to form the second seal;

the middle seal comprises glue; and said hub comprises at least one middle glue hole, located distally of the additional port and proximally of the inflation port and in communication with the distal hub channel, for supplying glue to the space between the wall of the distal hub channel and said catheter to form the middle seal.

26. The catheter assembly of claim 25, wherein the at least one proximal glue hole comprises a plurality of proximal glue holes, the at least one distal glue hole comprises a plurality of distal glue holes, and the at least one middle glue hole comprises a plurality of middle glue holes.

* * * * *